United States Patent
Behiels (10) Patent No.: US 9,615,805 B2
(45) Date of Patent: *Apr. 11, 2017

(54) IMAGE ALIGNMENT OF BREAST IMAGES

(71) Applicant: Agfa HealthCare NV, Mortsel (BE)

(72) Inventor: Gert Behiels, Mortsel (BE)

(73) Assignee: AGFA HEALTHCARE NV, Mortsel (BE)

( * ) Notice: Subject to any disclaimer, the term of this patent is extended or adjusted under 35 U.S.C. 154(b) by 167 days.

This patent is subject to a terminal disclaimer.

(21) Appl. No.: 14/375,007

(22) PCT Filed: Feb. 25, 2013

(86) PCT No.: PCT/EP2013/053691
§ 371 (c)(1),
(2) Date: Jul. 28, 2014

(87) PCT Pub. No.: WO2013/127730
PCT Pub. Date: Sep. 6, 2013

(65) Prior Publication Data
US 2015/0023576 A1   Jan. 22, 2015

Related U.S. Application Data

(60) Provisional application No. 61/603,504, filed on Feb. 27, 2012.

(30) Foreign Application Priority Data

Feb. 27, 2012  (EP) ..................................... 12157165

(51) Int. Cl.
*G06K 9/00* (2006.01)
*A61B 6/00* (2006.01)
(Continued)

(52) U.S. Cl.
CPC ............ *A61B 6/5235* (2013.01); *A61B 6/025* (2013.01); *A61B 6/03* (2013.01); *A61B 6/502* (2013.01);
(Continued)

(58) Field of Classification Search
CPC ......... G06T 2207/30068; G06T 7/0028; G06T 7/604
See application file for complete search history.

(56) References Cited

U.S. PATENT DOCUMENTS

2006/0050944 A1  3/2006  Takeo et al.
2006/0159321 A1  7/2006  Takeo et al.
(Continued)

FOREIGN PATENT DOCUMENTS

WO   WO 2011137409 A1 * 11/2011  ........... G06T 7/0012

OTHER PUBLICATIONS

R. Nevatia "Machine Perception" Ch 07 pp. 100-127 Prentice-Hall, Englewood Cliffs, New Jersy (1982).*
(Continued)

*Primary Examiner* — Bhavesh Mehta
*Assistant Examiner* — Ian Lemieux
(74) *Attorney, Agent, or Firm* — Keating and Bennett, LLP (57) ABSTRACT

A method of aligning at least two breast images includes aligning a relevant image part in each of the images, the relevant image parts being obtained on the basis of the result of a shape analysis procedure performed on the breast images.

7 Claims, 10 Drawing Sheets

(51) Int. Cl.
*G06T 7/00* (2017.01)
*G06T 7/60* (2017.01)
*A61B 6/02* (2006.01)
*A61B 6/03* (2006.01)

(52) U.S. Cl.
CPC .......... *G06T 7/0014* (2013.01); *G06T 7/0028* (2013.01); *G06T 7/604* (2013.01); *G06T 2207/10081* (2013.01); *G06T 2207/10116* (2013.01); *G06T 2207/30068* (2013.01)

(56) References Cited

U.S. PATENT DOCUMENTS

| | | | | |
|---|---|---|---|---|
| 2009/0257657 A1* | 10/2009 | Temmermans | ....... | G06T 3/0075 382/195 |
| 2013/0051676 A1* | 2/2013 | Wehnes | ................ | G06T 7/0012 382/190 |
| 2015/0003702 A1* | 1/2015 | Serlie | .................. | A61B 5/7275 382/128 |

OTHER PUBLICATIONS

L. Vincent, "Minimal path algorithms for the robust detection of linear features in images" in Mathematical Morphology and its Applications to Image and Signal processing, vol. 12 of Computational Imaging and Vision, Amsterdam, Kluwer, Proceedings for ISMM'98, Jun. 1998, pp. 331-338.*

Official Communication issued in International Patent Application No. PCT/EP2013/053691, mailed on Apr. 22, 2013.

Chen, "A Fast Classification Mask Construction Algorithm for Digital Mammograms", Journal of Convergence Information Technology, vol. 7, No. 1, Jan. 31, 2012, pp. 483-488.

Rangarajan et al., "A Robust Point Matching Algorithm for Autoradiograph Alignment", Visualization in Biomedical Computing: 4th International Conference, Sep. 22, 1996, pp. 277-286.

* cited by examiner

(a) RMLO (b) LMLO (c) RCC (d) LCC

IMAGE ALIGNMENT OF BREAST IMAGES

CROSS-REFERENCE TO RELATED APPLICATIONS

This application is a 371 National Stage Application of PCT/EP2013/053691, filed Feb. 25, 2013. This application claims the benefit of U.S. Provisional Application No. 61/603,504, filed Feb. 27, 2012, which is incorporated by reference herein in its entirety. In addition, this application claims the benefit of European Application No. 12157165.7, filed Feb. 27, 2012, which is also incorporated by reference herein in its entirety.

BACKGROUND OF THE INVENTION

1. Field of the Invention

The present invention relates to a method for image alignment of breast images.

2. Description of the Related Art

Radiologists examine mammographic images to diagnose various abnormalities in a breast. The images are nowadays examined on a display device such as the display screen of a computer workstation.

Essential for a mammographic display system is the ability of the radiologist to quickly analyze the mammographic images of the breast and create a report of his diagnosis.

Analyzing breast images often comprises comparing breast images by aligning two or more breast images. These images may be images of the same object acquired at different times and/or with different display settings or images of right and left breast etc.

Figure 2:
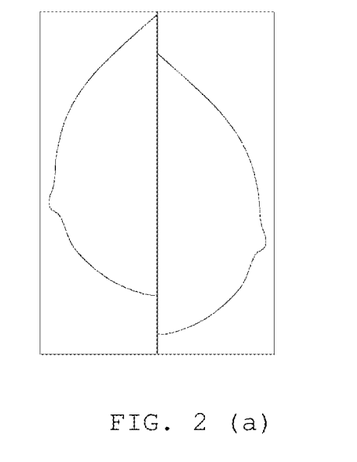
Figure 3:
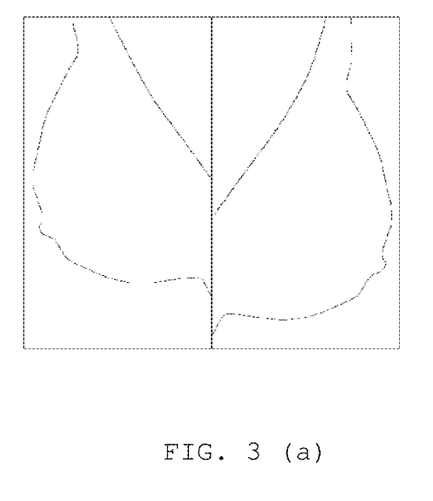
Figure 4:
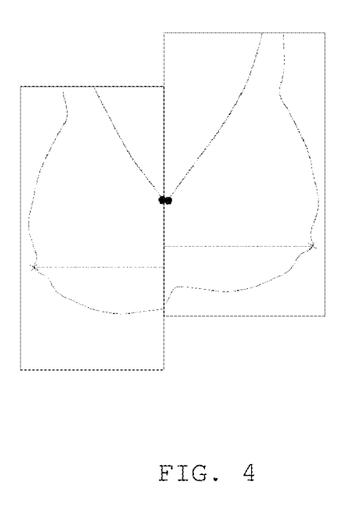
FIG. 4 shows pectoralis aligned MLO images for images where the image position differs (distance detector edge to chest).

The conventional procedure to achieve such an alignment is based on nipple alignment or pectoralis alignment. Mostly, for craniocaudal (CC) images, the nipple is located in each pair of images and the images are positioned such that the nipple is located at the same height (see FIG. 2). For mediolateral-oblique (MLO) images, either nipple or pectoralis alignment is used (see FIG. 3). While both methods generate similar results, it is possible that the alignment is different when the position of the breasts during the acquisition differs (see FIG. 4).

The observation that pectoralis alignment can be suboptimal in combination with the fact that accurate nipple detection is not always possible, is an indication that more robust alignment methods are desirable. Radiologists prefer aligned images because it facilitates comparison of the images. Aligned images are most similar to mirrored images for which our eyes and brains are trained to find differences. Alignment based on a few key features, being the nipple or the pectoralis muscle, is not optimal.

U.S. Pat. No. 7,885,443 as well as US 2011/0128289 disclose a method for facilitating temporal comparison of breast mammograms by a viewer. A first and a second mammogram are displayed at identical tissue distance per unit display distance in a number of display windows sized and paired according to a hanging protocol. A fiducial alignment marker location is identified in the breast tissue area of each of the mammograms. Paired ones of the displayed mammogram views are displayed horizontally adjacent to each other and are vertically aligned on said mammogram display according to said identified fiducial marker locations.

It is an aspect of the present invention to provide a method for optimal alignment of breast images so as to facilitate optimal analysis of breast images.

SUMMARY OF THE INVENTION

The above-mentioned aspects are realized by a method having the specific features set out below.

Specific features for preferred embodiments of the invention are also set out below.

Preferred embodiments of the present invention comprise alignment of breast images based on shape information of these breast images. By this method similar structures in mammograms may be placed at the same height.

The technique may be applied to align at least two images with different lateralities from the same patient but is also applicable to align images for temporal comparisons.

In one preferred embodiment a breast image is first segmented into a direct exposure or background region and foreground regions. From this segmentation, the skin boundary is determined. Optionally, the pectoralis muscle can be located. From these boundaries, only the relevant parts are retained. An example of a relevant part is the convex part of the skin boundary. To align two relevant parts, the parts are sampled and the points are aligned e.g. with the robust point matching technique.

In the context of the present invention the term 'mammographic image', 'mammogram' or 'breast image' refers to an image of a breast such as a radiation image of a breast. A radiation image of a breast in this invention is provided in the form of a (digital) signal representation wherein the signal values represent grey values of image pixels.

Further in the context of this application 'direct exposure area' or 'background area' means an area part of the radiation image of a breast in which radiation is not attenuated by the breast and has impinged directly onto a radiation detector used for recording the radiation image of the breast.

Also in the context of the present invention the term 'skin line estimate' (also referred to as 'skin line') is defined as the edge between the background area and the remainder of the mammographic image. This skin line is determined by a skin line extraction algorithm described below. The determined skin line may comprise pixels of the breast boundary as well as pixels not belonging to the breast boundary such as chest pixels, markers etc.

Several types of systems exist for generating a radiation image of a breast. Such systems are described furtheron.

Preferred embodiments of the present invention are generally implemented in the form of a computer program product adapted to carry out the method steps of the present invention when run on a computer. The computer program product is commonly stored in a computer readable carrier medium or device. Alternatively the computer program product takes the form of an electric signal and can be communicated to a user through electronic communication. Examples are one or more diskettes, compact disks, tapes, chips, wireless transmission means, internet transmission or downloading means etc. readable or accessible by computer for configurating and operating the computer when the storage media or device is read by the computer to perform the procedures described herein.

Further advantages and embodiments of the present invention will become apparent from the following description and drawings.

BRIEF DESCRIPTION OF THE DRAWINGS

FIG. 2 (a) shows left and right unaligned CC breast images.

FIG. 2 (b) shows nipple aligned CC breast images,

FIG. 3 (a) shows left and right unaligned MLO breast images.

FIG. 3 (b) shows nipple/pectoralis aligned MLO breast images.

FIG. 5 (a) shows for a star-shaped background search region the situation wherein all criteria are valid.

FIG. 5 (b) shows for a star-shaped background search region the situation wherein intensity criteria are not valid for angles between 12 and 3 o'clock.

FIGS. 6 (a) to (d) illustrate the segmentation of different clinical views.

FIG. 7 (a) illustrates the distance computation, FIG. 7 (b) illustrates the classification of points based on a threshold values set at −10.

FIGS. 8 (a) to (d) show extended skin lines which are classified as true breast boundary.

FIG. 9 (a) shows the initial position and correspondence.

FIGS. 9 (b) and (c) show the new position and correspondence after 1 or 2 iterations, respectively, of the deterministic annealing.

FIGS. 9 (d) and (e) illustrate intermediate steps.

FIG. 9 (f) shows the result after the convergence for M.

FIG. 10 (a) shows the situation in which the images are aligned according to the distance measure between the breast shape extracted from the images. The nipple is not perfectly aligned but general alignment of the breast is guaranteed.

FIG. 10 (b) shows that the general shape of the breasts are aligned which results in suboptimal pectoralis alignment but places similar breast structures at the same height.

DETAILED DESCRIPTION OF THE PREFERRED EMBODIMENTS

While the present invention will hereinafter be described in connection with preferred embodiments thereof, it will be understood that it is not intended to limit the invention to those embodiments.

Figure 1:
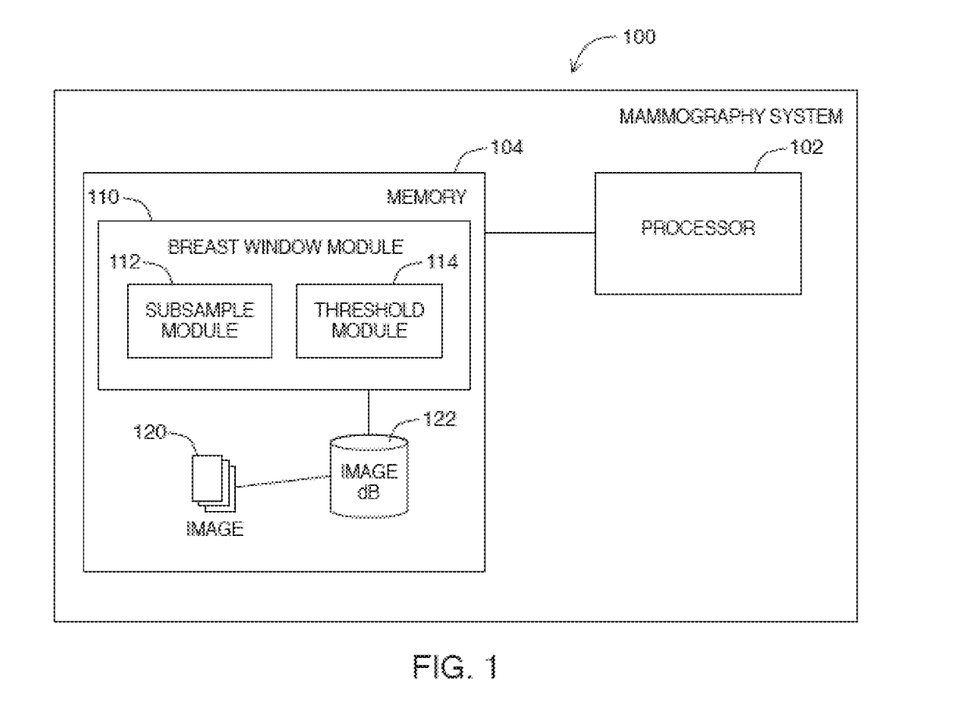
FIG. 1 shows a system in which a preferred embodiment of the present invention can be implemented.

FIG. 1 shows an example preferred embodiment of a mammography system 100. A mammography system 100 may contain a processor 102, operatively coupled to memory 104. Memory 104 stores a breast window module 110 for defining breast windows on images 120 stored on image database 122.

Images 120 stored on image database 122 may comprise mammography images. Those skilled in the art will appreciate that there are different types of mammography images such as craniocaudal (CC), containing a view of a breast as taken through the top of the breast and mediolateral oblique (MLO), containing a view of a breast as taken from the center of the chest to the lateral of the breast.

Various systems may be envisaged for acquiring a digital signal representation of a radiographic image of the breast such as projection radiography image acquisition systems, echography image acquisition systems, tomosynthesis systems, computed tomography systems etc.

Mammographic image acquisition systems typically comprise a radiation sensitive detector (e.g. x-ray radiation sensitive) for storing an image of an irradiated breast. Examples of suitable detectors are a radiographic film, a photo-stimulable phosphor screen, a direct radiography detector etc. A digital signal representation of the breast image is then obtained by reading out the image from the detector (e.g. by scanning the film, stimulating the photo-stimulable phosphor screen or reading out the direct digital detector) and eventually digitizing the read out signal. The digital signal representation of a mammographic image represents the grey value in each image pixel.

Image database 122 stores breast images 120, and may be implemented using any database software or persistent storage method known in the art. For example, image database 122 may be implemented using Oracle®, Microsoft SQL Server® or IBM DB2® with suitably defined schemas to identify and navigate images 120. In the exemplary embodiment, image database 122 may be part of a Picture Archiving and Communication Systems (PACS) deployment, such as those found in a hospital. While image database 122 is illustrated as residing in the same memory as mammography system 100, it will be understood that image database 122 may be stored and accessed remotely through a network connection, for example, using a Digital Imaging and Communications in Medicine (DICOM) protocol. In such case, it will be further understood that the operations of the breast window module 110 may be performed locally on the mammography system, remotely on the system where the image database 122 resides, or on a third-party system configured to access image database 122 and mammography system 100.

Segmentation

The first step of one preferred embodiment of the method of the present invention is a segmentation step which is applied to the digital signal representation of the rendered breast image. In this segmentation step a mask is created indicating direct exposure or background pixels. This segmentation step may also be omitted, e.g. when the gradient image derived from the breast image is used for further analysis.

This mask is in this preferred embodiment constructed in 2 steps: (1) an initial classification step and (2) a step for generation of a sequence of background masks from which the optimal background mask is selected. The optimal background mask is created by an iterative process in which the classification rules are strengthened in each iteration step.

First an initial mask of candidate background pixels is computed based on the grey pixel values in the rendered breast image. In this context the term 'rendered' refers to the image signal obtained by window/level setting and conversion to grey values. In the described exemplary preferred embodiment the rendering of the image uses the default, most conservative, window/level settings found in the DICOM tags associated with the image. The threshold is derived from the histogram of the image and selected such that typically all background pixels are selected with some additional non-background pixels.

Starting from this initial background mask, a sequence of further background masks is generated with a sequence of a so-called second thresholds th. The sequence of the second thresholds is in this preferred embodiment the initial gray level intensity for the local intensity variability within a search region.

Figure 5:
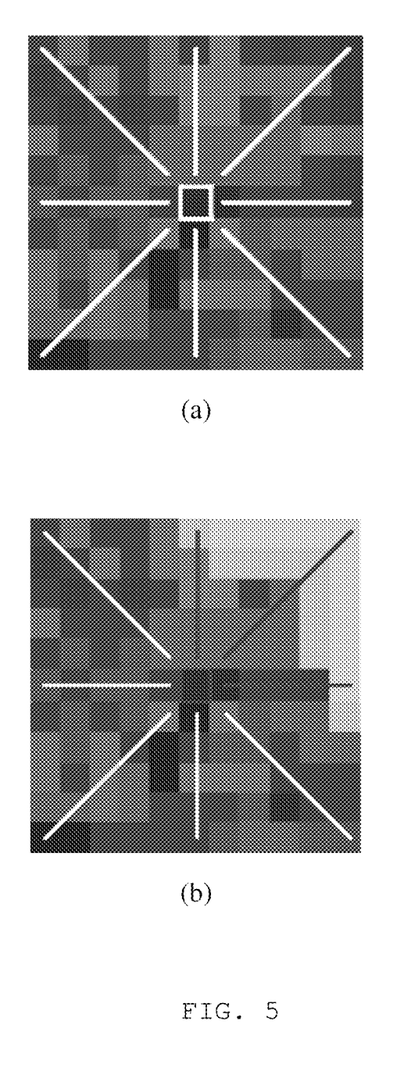

As illustrated in FIG. 5, the search region in the described preferred embodiment is defined as a star defining a number (in this embodiment: 8) radial search directions.

The difference between two successive masks is computed and used as a selection criterium for the most suitable background mask. As a measure of this selection criterium the difference is used between the number of background pixels in the 2 masks. The final background mask is the mask which shows minimum difference with the next mask in the sequence of segmentation masks.

Alternative forms of search regions (other forms or patterns of search area) and selection criteria may be envisaged.

Preferably each image in the sequence for a specified threshold th, is computed using the following classification rules for all pixels i:

1. the pixel must be a candidate background pixel in the initial background mask
2. there is no pixel at a distance of 2 pixels which is not an initial background pixel
3. no pixel is found along one of 8 search directions radiating outwards of pixel i which exceeds a varying threshold $t_{var}$ over a fixed distance. $t_{var}$ is initialized with the intensity value of pixel i scaled with the specified threshold th for the mask in the sequence. The varying threshold $t_{var}$ is adjusted with a fraction of the central intensity value at pixel i. The fraction with which $t_{var}$ is adjusted may also be dependent on the intensity value of the pixel under investigation. E.g. the update can be smaller if the pixel under investigation is smaller than the intensity value for the central pixel.

As an additional step, small or irregular regions within the optimal background mask can be identified and removed.

Figure 6:
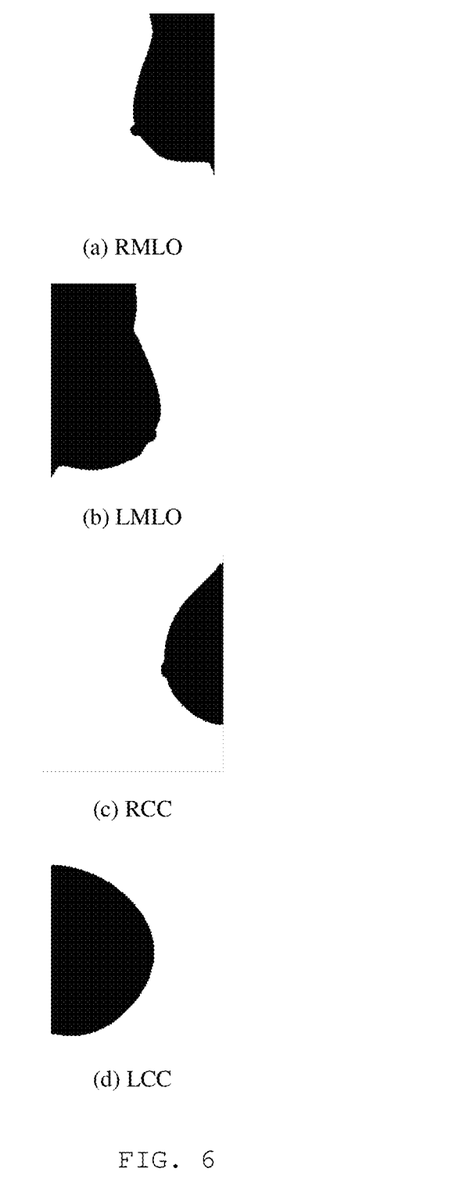

Some results of the segmentation algorithm are shown in FIG. 6.

Skin-Line

Figure 8:
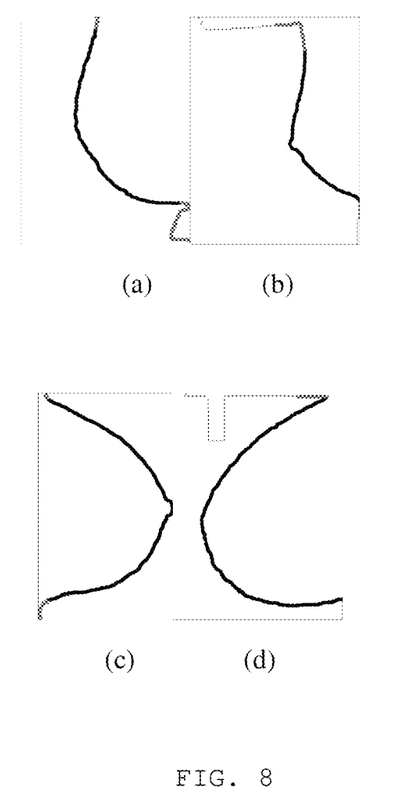

Having segmented the image into a background and foreground region, in the next step of the described preferred embodiment a skin line boundary is found by applying a minimal cost path technique to the selected optimal mask defining direct exposure pixels. The cost for pixels on the edge of the direct exposure area are set to a low value e.g. 2 and the cost to traverse any other pixel is set to a high value e.g. 255. With standard dynamic programming techniques it is easy to find a path from the bottom of the image located at the side of the breast to the top of the image. Some extracted skin-lines are also shown in FIG. 8.

Having found the skin-line, points of the skin-line are classified as a point belonging to the breast boundary by computing and evaluating a measure which is an indication of convexity and evaluating this measure with regard to a given tolerance value.

The measure is computed as follows:

1. Take one point from the set of skin-line points,
2. Take a second point located a fixed number positions further in the set of skin-line points,
3. Connect these two points with an imaginary line,
4. Compute the signed distance for all intermediate points on the skin-line with this imaginary line,
5. Mark both points as convex points if the minimum of the signed distance of all intermediate points of step 4 is greater than 0
6. Mark each point as extension point if the signed distance is larger than a defined threshold and the point is not already marked as breast point.

Figure 7:
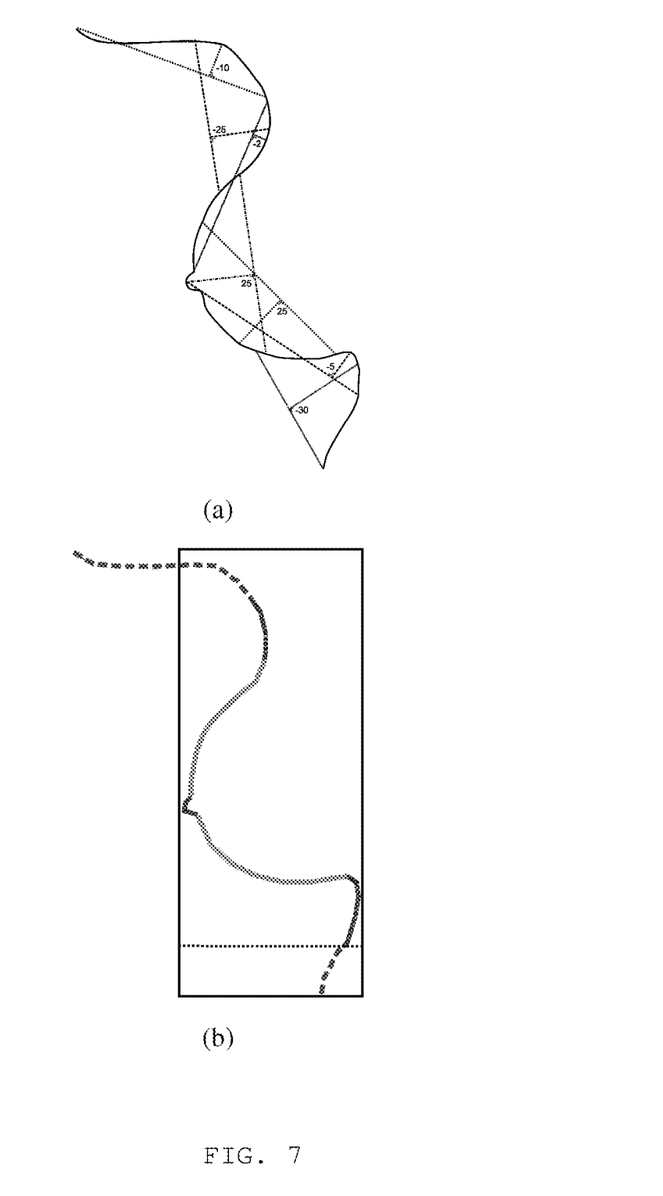

The above algorithm is illustrated in FIG. 7a. The final breast boundary is then determined as the segment of convex and extension points containing the longest segment of convex points. In the example of FIG. 7b, the threshold is set to a minimum of −10.

Alternatives for the above described shape analysis method may be envisaged such as analysis of curvature, of Fourier descriptors, of curvelets, Eigenshape analysis/PCA (Principal Component analysis) etc.

Alternative methods may be envisaged for determining the skin line estimate in general such as identifying border points of the largest object in the image etc.

The above-described segmentation algorithm may be omitted, e.g. if the minimum cost path analysis is applied to the gradient image deduced from the radiation image of the breast.

Alignment

Once the breast boundaries are found, they need to be aligned. To align the breast images, only the vertical offset is needed. To determine this offset a more general transformation is searched in this preferred embodiment such as an affine transformation and only the parameter determining this vertical offset is used.

In the context of the present invention, a more general transformation is a transformation that generates more than only a vertical offset value.

Examples are a transformation that results in a vertical and horizontal alignment, or vertical and horizontal alignment combined with scaling and/or rotation, an affine transformation.

Also possible are a transformation which generates a vertical and horizontal alignment component and a non-rigid component or all above-described combinations with an additional non-rigid component.

It is also possible to apply a transformation which only generates a vertical component.

The problem of finding the optimal transformation between 2 boundaries can be reduced to a minimization problem (see reference [3]). Denote the boundary points from boundary P and boundary Q, $P_i=(x_i,y_i)$, i=1, 2, ..., $N_p$ and $Q_j=(x_j,y_j)$, j=1, 2, ..., $N_q$ respectively. $N_p$ and $N_q$ are the number of points. The robust point matching (RPM) algorithm minimizes the following objective function:

$$\min_{M,\theta,t,s} E(M,\theta,t,s) = \qquad (1)$$

$$\sum_{i=1}^{N_p}\sum_{j=1}^{N_q} M_{ij} \|P_i - t - sR(\theta)Q_j\|^2 + \underbrace{\frac{\gamma}{2}(\log s)^2}_{scale\ regularization} - \underbrace{\alpha \sum_{i=1}^{N_p}\sum_{j=1}^{N_q} M_{ij}}_{outlier\ regularization}$$

subject to $$\sum_{i=1}^{N_p+1} M_{ij} = 1 \ \forall j \in \{1,\ldots,N_q\}, M_{ij} \in \{0,1\} \qquad (2)$$

$$\sum_{j=1}^{N_q+1} M_{ij} = 1 \ \forall i \in \{1,\ldots,N_p\}, M_{ij} \in \{0,1\}$$

$$M_{ij} = \begin{cases} 1 & \text{if point } P_i \text{ corresponds to } Q_j \\ 0 & \text{otherwise} \end{cases} \qquad (3)$$

$$M_{i(N_q+1)} = \begin{cases} 1 & \text{if point } P_i \text{ is an outlier} \\ 0 & \text{otherwise} \end{cases}$$

$$M_{(N_p+1)j} = \begin{cases} 1 & \text{if point } Q_j \text{ is an outlier} \\ 0 & \text{otherwise} \end{cases}$$

Equation 1 describes an optimization problem from which the transformation parameters—translation t, rotation angle θ and scale s—can be obtained by minimization. γ is a regularization parameter which controls the degree of departure of the scale parameter from unity. Equation 1 also sets up an optimization problem on the point correspondences through the correspondence variables $M_{ij}$. The variable $M_{ij}$ is a correspondence variable which indicates when correspondences between points have been found or outliers are discarded. The degree of robustness is enforced by the parameter α. If α is large, fewer points are discarded and vice-versa. An example of correspondence matrix is shown in Table 1.

| $M_{i,j}$ | $X_1$ | $X_2$ | $X_3$ | $X_4$ | outlier |
|---|---|---|---|---|---|
| $Y_1$ | 1 | 0 | 0 | 0 | 0 |
| $Y_2$ | 0 | 1 | 0 | 0 | 0 |
| $Y_3$ | 0 | 0 | 0 | 0 | 1 |
| outlier | 0 | 0 | 1 | 1 | |

Table 1: An example of the correspondence matrix. Points $x_1$ and $x_2$ correspond to $y_1$ and $y_2$ respectively. The rest of the points are outliers.

To overcome the difficulty in jointly solving for the spatial mapping and the correspondences, the approach of ref. [3] can be followed. The Birkhoff-von Neumann theorem states that "the set of (N×N) doubly stochastic matrices is the convex hull of the set of (N×N) permutation matrices" (ref. [1]). A doubly stochastic matrix is a square matrix with all positive entries and rows and columns summing to one. Following the Birkhoff-von Neumann theorem, we relax the correspondence matrix constraints from permutation matrix constraints to doubly stochastic matrix constraints. The row and column constraints are enforced using Lagrange parameters and the positivity constraint via a barrier function ([2]):

$$E(M, \theta, t, s, \mu, \nu) = \sum_{i=1}^{N_p} \sum_{j=1}^{N_q} M_{ij} \|P_i - t - sR(\theta)Q_j\|^2 + \frac{\gamma}{2}(\log s)^2 - \quad (4)$$

$$\alpha \sum_{i=1}^{N_p} \sum_{j=1}^{N_q} M_{ij} + \underbrace{\sum_{i=1}^{N_p} \mu_i \left( \sum_{j=1}^{N_q+1} M_{ij} - 1 \right) + \sum_{j=1}^{N_q} \nu_j \left( \sum_{i=1}^{N_p+1} M_{ij} - 1 \right)}_{\text{Lagrange parameters}} +$$

$$\underbrace{\frac{1}{\beta} \sum_{i=1}^{N_p+1} \sum_{j=1}^{N_q+1} M_{ij} \log M_{ij}}_{\text{barrier function for positivity constraint}}$$

Fixing the spatial mapping, we can solve for the correspondence matrix M in the above objective function. Minimizing Eq. 4 w.r.t. M, we get $$M_{ij} = \exp[-\beta(\|P_i - t - sR(\theta)Q_j\|^2 - \alpha + \mu_i + \nu_j) - 1]$$
$$M_{i(N_q+1)} = \exp[-\beta \mu_i - 1]$$
$$M_{(N_p+1)j} = \exp[-\beta \nu_j - 1]$$

$$\forall\, i \in \{1, \ldots, N_p\}$$
$$\forall\, j \in \{1, \ldots, N_q\}$$
$$\forall\, i \in \{1, \ldots, N_p\}$$
$$\forall\, j \in \{1, \ldots, N_q\}$$

Solving for the two Lagrange parameters using a gradient ascent approach is likely to be slow and inefficient. Now solving for the Lagrange parameters by alternating between solving for μ and then ν rather then steepest ascent is identical to Sinkhorn's algorithm (except for the added benefit of the outliers) ([4]). Sinkhorn's theorem states that "a doubly stochastic matrix is obtained from any square matrix with positive entries by the simple process of alternating row and column normalizations".

[3] refers to the barrier function control parameter β as the inverse temperature and the update of the matrix elements $M_{ij}$ as the soft assign. β is slowly increased according to an annealing schedule. As the deterministic annealing parameter β is increased, the correspondence matrix entries approach binary values. Outlier rejection occurs in the limit when β→∞ with the outliers becoming binary valued. Since the entire process is deterministic, they refer to the overall approach as deterministic annealing.

The spatial mapping parameters are updated with the correspondence matrix held fixed. Closed-form solutions are obtained for the rotation and translation parameters by equating to zero the partial derivatives of E(M,θ,t,s) w.r.t. to each parameter. The scale parameter is set using a few iterations of Newton's method.

The pseudo code of the Robust Point Matching (RPM) algorithm is:

- Initialize θ = 0, s = 1, t = 0, β = $β_0$, $M_{ij}$ = 1 + $ε_{ij}$
- Deterministic annealing in β
  - Repeat until convergence for M
    - Soft assign
      $\forall i \in \{1, \ldots, N_p\}, \forall j \in \{1, \ldots, N_q\}$
      $\Delta_{ij} \leftarrow -\|P_i - t - sR(\theta)Q_j\|^2 + \alpha$
      $M_{ij} \leftarrow \exp(\beta \Delta_{ij})$
    - Sinkhorn's algorithm: Update M by alternating normalization of the rows and columns $$M_{ij} \leftarrow \frac{M_{ij}}{\sum_{j=1}^{N_q+1} M_{ij}}$$

$$M_{ij} \leftarrow \frac{M_{ij}}{\sum_{i=1}^{N_p+1} M_{ij}}$$
    - Update spatial mapping
  - Increase β

Figure 9:
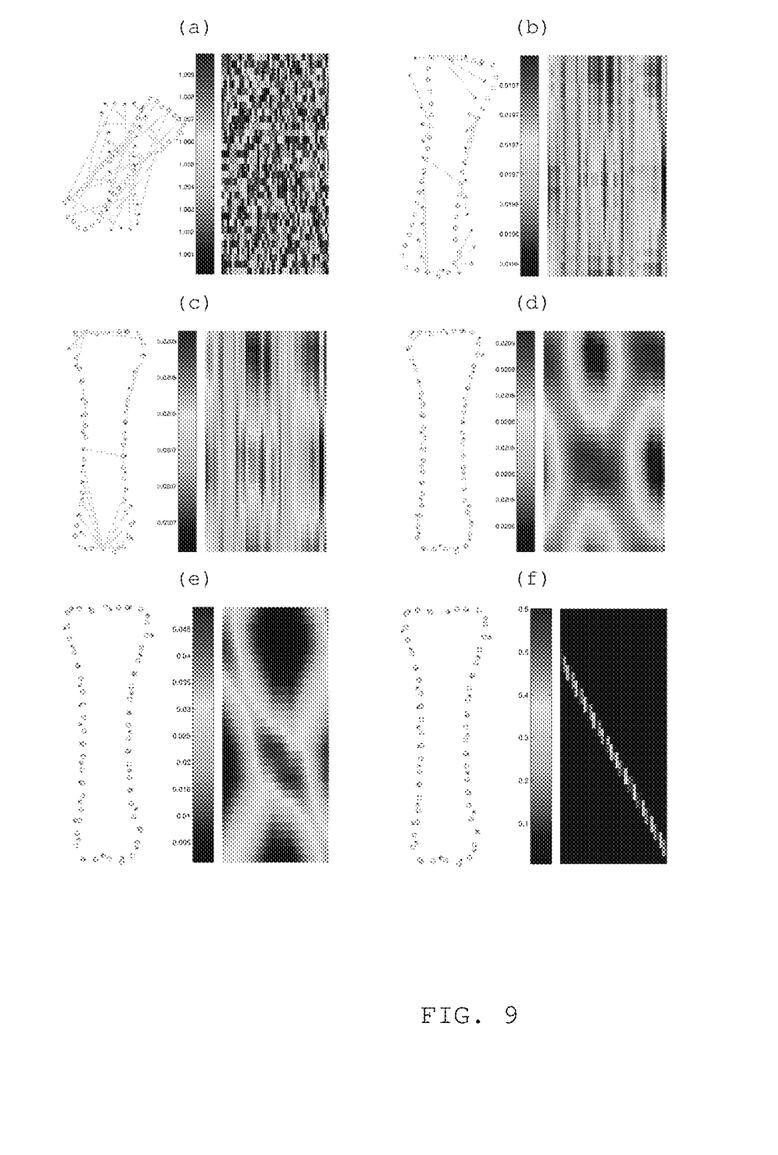
FIG. 9 shows the results of the first annealing step of the Robust Point Matching algorithm.

$ε_{ij}$ are small random variables. The algorithm is illustrated in FIG. 9 for the alignment of 2 bones in the hand.

The advantage of the RPM algorithm is that it allows to align 2 two boundary sets with a different number of points. It also is robust to missing parts (eg. missing pectoralis muscle boundary).

Figure 10:
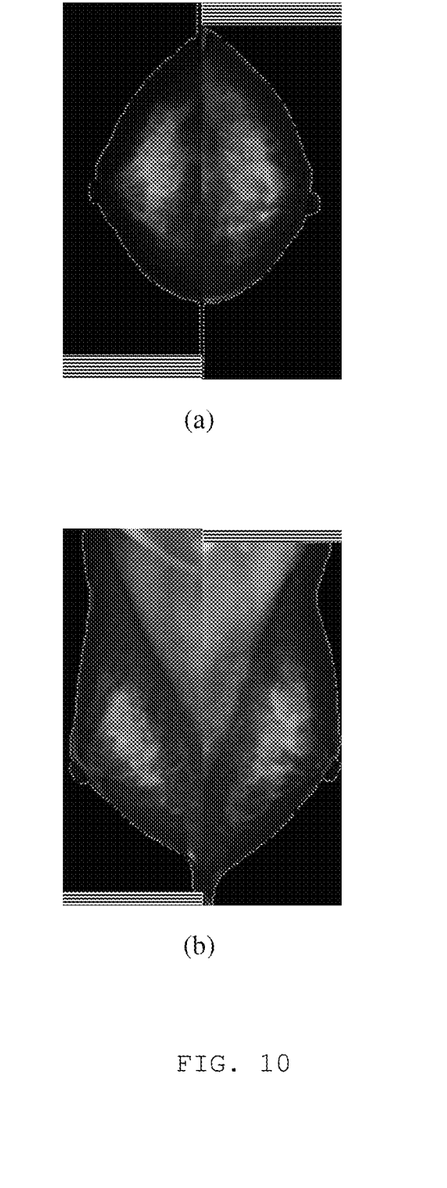
FIG. 10 illustrates breast aligned images obtained by a preferred embodiment of the present invention showing better results than obtained by nipple or pectoralis alignment.

FIG. 10 shows results of the technique applied to align the extracted breast boundaries. This example is especially selected to demonstrate that this method does not align the nipple or pectoralis. The results demonstrated in FIG. 10 are very much suitable for image comparison compared to nipple or pectoralis aligned images.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The following references have been referred to:

[1] J. J. Kosowsky and A. L. Yuille. The invisible hand algorithm: solving the assignment problem with statistical physics. Neural Netw., 7(3):477-490, 1994.

[2] D. G. Luenberger. Linear and nonlinear programming. Addison-Wesley, 2nd edition, 1984.
[3] A. Rangarajan, H. Chui, E. Mjolsness, S. Pappu, L. Davachi, P. Goldman-Rakic, and J. Duncan. A robust point matching algorithm for autoradiograph alignment. Medical Image Analysis, 4(1), 1997.
[4] Anand Rangarajan, Steven Gold, and Eric Mjolsness. A novel optimizing network architecture with applications. Neural Computation, 8(5):1041-1060, 1996.

The invention claimed is:

1. A method of aligning at least two breast images, the method comprising the steps of:
   extracting in each of the at least two breast images a relevant image portion by determining a skin line in each of the at least two breast images, and subjecting the skin lines to a shape analysis procedure including an evaluation of a measure of convexity relative to a given tolerance value; and
   aligning the relevant image portions; wherein
   each of the relevant image portions includes convex points of the skin line, wherein points of the skin line are classified as convex points by applying the steps of:
      for a first point in a set of points of the skin line considering a second point in the set of points;
      connecting the first point and the second point with an imaginary line;
      computing a signed distance from each of a plurality of intermediate points to the imaginary line, the plurality of intermediate points being included in the set of points of the skin line and on the skin line between the first point and the second point; and
      marking the first point and the second point as convex points if a minimum of the signed distance from each of the plurality of intermediate points to the imaginary line is greater than 0.

2. The method according to claim 1, wherein the skin line is obtained by the steps of:
   segmenting one of the at least two breast images to create a mask indicating pixels of a direct exposure area; and
   subjecting the mask to a minimal cost path technique.

3. The method according to claim 1, wherein the step of aligning the relevant image portions is a vertical alignment.

4. The method according to claim 3, wherein the vertical alignment is derived from a general transformation which generates other components in addition to a vertical alignment component.

5. The method according to claim 4, wherein the transformation is an affine transformation.

6. The method according to claim 5, wherein the affine transformation is estimated with a robust point matching technique.

7. A non-transitory computer readable medium including computer executable program code for carrying out, when the computer executable program code is executed on a computer, the steps of claim 1.

* * * * *